Figure 1:
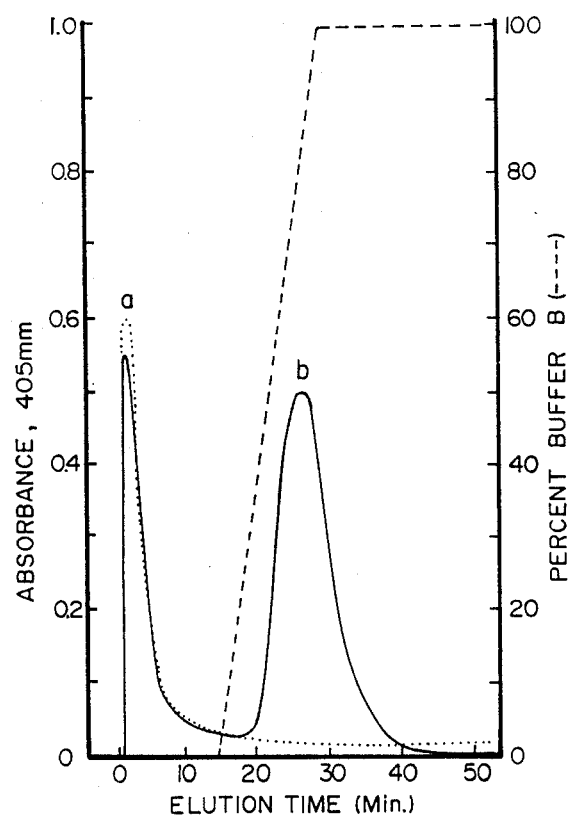

United States Patent [19]

Hsia

[11] Patent Number: 4,925,574

[45] Date of Patent: May 15, 1990

[54] PURIFICATION OF HEMOGLOBIN AND MODIFIED HEMOGLOBIN BY AFFINITY CHROMATOGRAPHY

[75] Inventor: Jen-chang Hsia, Concord, Canada

[73] Assignee: Canadian Patents & Development Limited, Canada

[21] Appl. No.: 839,539

[22] Filed: Mar. 14, 1986

[30] Foreign Application Priority Data

Jun. 26, 1985 [CA] Canada .................................... 485392

[51] Int. Cl.$^5$ ............................................. B01D 15/08
[52] U.S. Cl. .................................... 210/635; 210/656;
530/385; 530/413; 530/417
[58] Field of Search ....................... 530/385, 413, 417;
210/635, 656, 198.2

[56] References Cited

U.S. PATENT DOCUMENTS

| Re. 32,011 | 10/1985 | Zimmerman | 530/413 |
|---|---|---|---|
| 3,350,174 | 10/1967 | Mattenheimer | 210/635 |
| 3,873,514 | 3/1975 | Chu | 210/635 |
| 3,917,527 | 11/1975 | Shaltiel | 210/635 |
| 4,011,377 | 3/1977 | Dean | 530/413 |
| 4,143,203 | 3/1979 | Rigopulas | 528/502 |
| 4,168,300 | 9/1979 | Andersson | 530/413 |
| 4,282,352 | 8/1981 | Imahuri | 536/27 |
| 4,330,440 | 5/1982 | Ayers | 210/635 |

FOREIGN PATENT DOCUMENTS 2652636  5/1978  Fed. Rep. of Germany ...... 530/417

OTHER PUBLICATIONS

"Separation of Glyoxylated Hemoglobin with Varying Affinity by Polyanion Fast Protein Liquid Chromatography", by J. Carleton Hsia et al, Journal of Chromatography, 303(1984), 425-428.
"Preparation and Properties of Hemoglobin Modified with Derivatives of Pyridoxal", by Rein Hold Benesch and Ruth E. Benesch, Methods in Enzymology, vol. 76, pp. 147-159.
"Triphosphate Spin-Lable Studies of Allosteric Interactions in Hemoglobin", By R. Ogata, et al, pp. 56-57.
"The Effect of Organic Phosphates from the Human Erythrocyte on the Allosteric Properties of Hemoglobin", by Reinhold Benesch and Ruth E. Benesch, Biochemical and Biophysical Research Communications, vol. 26, No. 2, 1967.
"X-Ray Diffraction Study of Binding of 2,3-Diphosphoglycerate to Human Deoxyhaemoglobin", by Arthur Aronone, Nature, vol. 237, May 19, 1972, pp. 146-149.
"Interacellular Organic Phosphates as Regulators of Oxygen Release byHaemoglobin", by Reinhild Benesch and Ruth E. Benesch, Nature, vol. 221, Feb. 15, 1969, pp. 618-622.
"Current Status of Erythrocyte Substitutes", by George P. Biro, Can Med Assoc J., vol. 129, Aug. 1, 1983.
Benesh, "Labeling of Hemoglobin with Pyridoxal Phosphate", vol.2 57, No. 3, Feb. 1982, pp. 1320-1324.

*Primary Examiner*—Ernest G. Therkorn
*Attorney, Agent, or Firm*—Nixon & Vanderhye

[57] ABSTRACT

The invention disclosed relates to a method for the purification of hemoglobin by the technique of affinity chromatography. Contrary to current belief, the binding of oxygen and selected polyanions to hemoglobin is not mutually exclusive. The novel method comprises immobilizing a polyanion which specicically binds hemoglobin via its polyanion binding site, on a chromatographic gel and passing the hemoglobin containing solution or mixture through the gel. The hemoglobin is thus retained in the gel, while impurities are eluted from the gel. The novel method is also applicable to the separation of unmodified hemoglobin from a liquid reaction mixture containing modified and unmodified hemoglobin.

26 Claims, 2 Drawing Sheets

PURIFICATION OF HEMOGLOBIN AND MODIFIED HEMOGLOBIN BY AFFINITY CHROMATOGRAPHY

The invention relates to hemoglobin-based acellular oxygen carriers, and more specifically to the purification of hemoglobin and modified hemoglobin by the technique of affinity chromatography.

Research in the development of an acellular oxygen-carrying solution for use as a blood substitute has been in two areas, involving solutions of hemoglobin-based and perfluorocarbon substances, as described for example by Biro (Can. Med. Assoc. J., Vol. 129, 1983, pp. 237-244). Recent work has indicated that the perfluorocarbons are less suitable due, for example, to the special clinical conditions needed for their use and to problems of toxicity. Present research is therefore focussed on potential hemoglobin-based blood substitutes. Since hemoglobin in solution (instead of in the red cell where it is naturally found) does not act as a physiologically satisfactory oxygen carrier, the development of hemoglobin derivatives with good oxygen-carrying and circulatory characteristics is warranted.

The principal source of hemoglobin for this research is presently "outdated" donor blood. Red blood cells are naturally rich in hemoglobin. Isolation of hemoglobin from this source has been accomplished by a number of methods involving the separation of hemoglobin from other red cell cytoplasmic proteins and from the cell stroma.

The present technique for purification of hemoglobin is by ion-exchange chromatography. This technique has been widely used in analytical and diagnostic applications. (See for example Benesch and Benesch, Meth. Enzymol., Vol. 76, pp. 174-179, 1981 and Hsia et al., J. Chromatog., Vo. 303, pp. 425-428, 1984.)

A much more rapid and specific purification technique, however, is affinity chromatography, which selectively isolates biomolecules by virtue of their binding specificity for particular molecules called ligands. Generally in this technique, the ligand is immobilized on a chromatographic gel, and a solution containing the molecule of interest is passed through the gel. The molecule of interest is retained in the gel by virtue of its specific binding of the ligand, while the other components present in the solution are eluted.

It is known that hemoglobin specifically binds small polyanionic molecules, especially 2,3-diphosphoglycerate (DPG) and adenosine triphosphate (ATP), present in the mammalian red cell (Benesch and Benesch, Nature, Vol. 221, p. 618, 1969). This binding site is located at the centre of the tetrameric structure of hemoglobin (Arnone, A., Nature, Vol. 237, p. 146, 1972). The binding of these polyanionic molecules is important in regulating the oxygen-binding affinity of hemoglobin since it allosterically affects the conformation of hemoglobin leading to a decrease in oxygen affinity (Benesch and Benesch, Biochem. Biophys. Res. Comm., Vol. 26, p. 162, 1967). Conversely, the binding of oxygen allosterically reduces the affinity of hemoglobin for the polyanion. (Oxy)hemoglobin therefore binds DPG and ATP weakly. This is shown, for example, by studies of spin-labelled ATP binding to oxy- and deoxyhemoglobin as described by Ogata and McConnell (Ann. N.Y. Acad. Sc., Vol. 222, p. 56, 1973). In order to exploit the polyanion-binding specificity of hemoglobin, or indeed to perform any adjustment of its oxygen-binding affinity by chemically modifying the polyanion binding site, it has been necessary in the prior art that hemoglobin be deoxygenated. However, hemoglobin as it exists in solutions or mixtures exposed to air is in its oxy state, i.e. (oxy)hemoglobin. In fact it is difficult to maintain hemoglobin solutions in the deoxy state, (deoxy)hemoglobin, throughout a chromatographic procedure. Because of these difficulties, the technique of affinity chromatography has not been used in the prior art to purify hemoglobin.

Unexpectedly, applicant has found that (oxy)hemoglobin may be isolated and purified by applying the technique of affinity chromatography.

The invention comprises the use of affinity chromatography for the isolation and purifiction of (oxy)hemoglobin from whole blood or other sources or mixtures, by virtue of reversible binding of hemoglobin via its polyanion binding site to a polyanion immobilized on a chromatographic gel support.

According to the invention, a method for the isolation of (oxy)hemoglobin from (oxy)hemoglobin-containing solutions or mixtures is provided, comprising:

(a) immobilizing a polyanion which specifically binds hemoglobin via its polyanion binding site, on a chromatographic gel; and (b) passing the (oxy)hemoglobin-containing solution or mixture through the gel, whereby the (oxy)hemoglobin is retained in the gel, while other components of the solution or mixture are eluted.

More specifically, if (oxy)hemoglobin solutions are passed through ATP-agarose gels (commercially available or prepared by known methods) it is observed that hemoglobin is retained by the gel, resulting in a so-called "red gel". The oxygen-binding characteristics of hemoglobin in the red gels, as demonstrated by the oxygen dissociation curve, are similar to those of its soluble ATP complex ($P_{50} \simeq 35$ mmHg) rather than of hemoglobin in Bis-Tris buffer solution ($P_{50} \simeq 7$ mmHg). Hemoglobin in the red gel is therefore allosterically modified by ATP binding to the polyanion binding site. As further evidence of this, the introduction of a solution containing any of a variety of competing anions causes elution of hemoglobin from the gel. Some of these competing anions, in order of decreasing effectiveness, are inositol hexaphosphate $>$ ATP $\simeq$ pyridoxal phosphate $\simeq$ DPG $>$ adenosine diphosphate $>$ phosphate ion chloride ion. This specific and reversible binding, in addition to the oxygen dissociation kinetics of the red gel, represents a functional demonstration of the specific binding of (oxy)hemoglobin to the polyanion affinity gel.

This finding, which contradicts literature reports of the mutually exclusive binding of oxygen and polyanions to (oxy)hemoglobin, is attributed to the following. Firstly, the ATP-agarose gel presents to the hemoglobin a high local concentration of ATP, stoichiometrically favouring binding. Secondly, it is believed that the hydrophobic spacer molecule which links ATP to the gel, and the agarose gel material itself, acts to enhance ATP binding to the polyanion-binding site of hemoglobin.

Thus, the technique of affinity chromatography can be applied to the isolation and purification of (oxy)hemoglobin. This represents an improvement upon conventional techniques in that it specifically isolates hemoglobin of high purity in a one-step chromatographic procedure, using gentle conditions which do not disrupt the native structure of the protein. It is readily adapted to large-batch preparations, as will be necessary for scaled-up production of hemoglobin-based blood substitutes. Finally, in terms of the functional quality of the product, this procedure selectively isolates hemoglobin with its ability to bind polyanions intact, giving functionally intact hemoglobin while at the same time eliminating undesirable contaminants.

In the preferred form of this aspect of the present invention, (oxy)hemoglobin is isolated by affinity chromatography on affinity gels comprising a polyanionic molecule linked by a hydrophobic spacer group (cross-linking agent) to a chromatographic gel support by known methods. Examples of polyanionic ligands are diphosphoglycerate, nucleoside phosphates, inositol phosphates and sulphates, etc. Examples of cross-linking agents or spacers are adipic acid and diaminohexane. Examples of chromatographic gel supports are agarose and silica gels.

The chromatographic procedure is as follows. A solution containing (oxy)hemoglobin and other components, e.g. red cell cytoplasmic proteins, in equilibrium with air, is injected into the affinity gel and eluted under conditions which favour hemoglobin binding to the gel, according to the known practices of affinity chromatography. Ultimately the non-hemoglobin components are eluted from the gel and hemoglobin is retained, causing the gel to appear red. Conditions are then changed to favour dissociation of hemoglobin from the gel, and it is eluted as a pure hemoglobin fraction. The preferred condition for elution of hemoglobin from the gel is the use of a buffer containing an anion which competes with the polyanionic moiety of the affinity gel for specific binding to hemoglobin, thus displacing it from the gel. The buffer is one which does not affect the binding of hemoglobin to the polyanion moiety. Bis-Tris buffer, pH 7.0 has been found suitable.

According to another aspect of the invention, applicant's hemoglobin purification technique can be applied to the removal of residual unmodified hemoglobin from liquid reaction mixtures containing modified and unmodified hemoglobin following chemical modification of the hemoglobin to improve its oxygen-carrying and circulatory characteristics. The reactions involved in modifying hemoglobin are typically incomplete and result in a mixture of modified and unmodified hemoglobin fractions. Residual unmodified hemoglobin poses problems in vivo due to excessive oxygen-binding affinity, its rapid excretion from the circulation, and possibly vasoconstrictor activity. Although this unmodified hemoglobin is currently removed from modified hemoglobin containing reaction mixtures on an analytical scale by ion-exchange chromatography, it is generally not removed in large-scale preparations.

It will be apparent hereinafter that applicant's technique is capable of removing residual unmodified hemoglobin from modification reaction mixtures on a preparative scale, thus comprising an important quality-control step in the modification of hemoglobin as a starting material for the preparation of acellular oxygen-carrying solutions.

More specifically, modified hemoglobin is considered here to mean purified, acellular hemoglobin to whose polyanion binding site a DPG analogue has been covalently attached by any of several known methods, or by any other method, for the purposes of (a) stabilizing the native tetrameric structure of hemoglobin in solution, and (b) allosterically lowering the oxygen-binding affinity of hemoglobin, simulating the regulation which is performed naturally in the red blood cell by DPG or its naturally occurring analogues, e.g. ATP, inositol pentaphosphate, etc.

The reaction mixture, comprising the product of the modification reaction, is assumed to contain modified hemoglobin and residual, unmodified hemoglobin which remains due to the incomplete nature of the modification reaction.

The reaction mixture is passed through the polyanion affinity column according to the known procedures of affinity chromatography. In the unmodified hemoglobin molecule, the polyanion binding site is unoccupied and the molecule is therefore retained by the gel via specific binding of the polyanion moiety of the gel to this site. Conversely, in the modified hemoglobin molecule the polyanion binding site is by definition occupied by the covalently attached polyanion or other modifying agent. Modified hemoglobin therefore will not bind specifically to the gel, and is eluted as the unretained fraction.

Thus polyanion affinity chromatography is capable of readily separating hemoglobin from non-hemoglobin components in a mixture according to the first aspect of the invention, and is also capable of separating modified from unmodified hemoglobin, regardless of the modification procedure used, on the basis of the state of the polyanion binding site. This allows purification of hemoglobin, especially from unconventional sources where the use of conventional purification techniques is not feasible, and also allows preparation of an essentially pure modified hemoglobin fraction by adding one chromatographic step to any of several known modification procedures.

In the drawing which illustrates the preferred embodiments of the invention:

FIG. 1. Elution profile of hemoglobin chromatographed on an ATP-agarose affinity column.

Chromatogram of 10 ul (50 ug) of SFH on an analytical capillary column packed with 10 ul of AGATP gel. Elution of SFH by buffer A (50 mM Bis-Tris buffer, pH 7.0) shows only peak a, the unretained fraction (dotted line). Introduction of a gradient of buffer B (10 mM ATP in buffer A; gradient shown as broken line) results in the elution of a retained fraction, peak b (solid line). Experimental conditions were: flow rate 0.1 ml/min, temperature approximately 20° C., using a FPLC chromatographic system (Pharmacia Model LCC 500).

Figure 2:
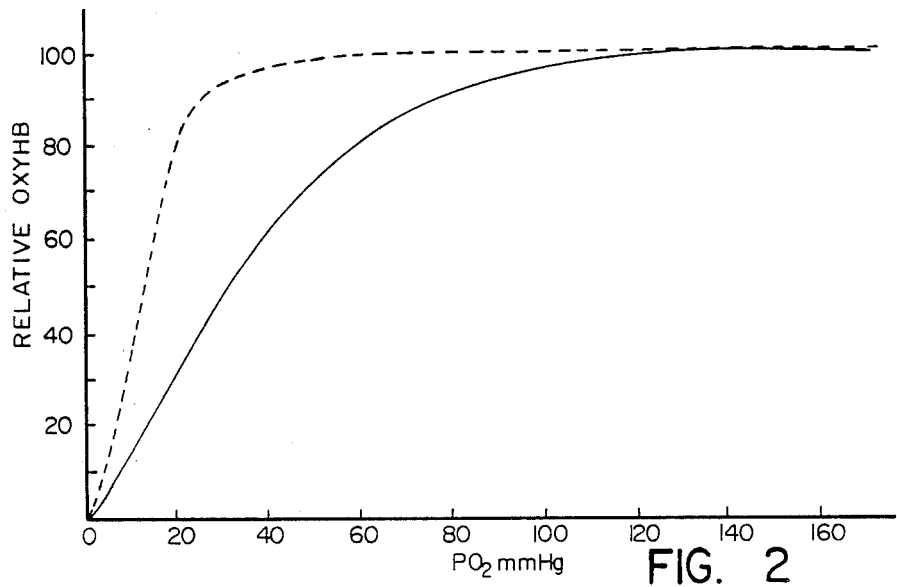

FIG. 2. Modification of the oxygen affinity of SFH by AGATP gel.

Oxygen dissociation curve of SFH in the presence of AGATP gel (solid line) and plain agarose gel (broken line) in 50 mM Bis-Tris buffer, pH 7.0, at 37° C. Curves were obtained using a Hem-O-Scan oxygen dissociation analyzer.

Figure 3:
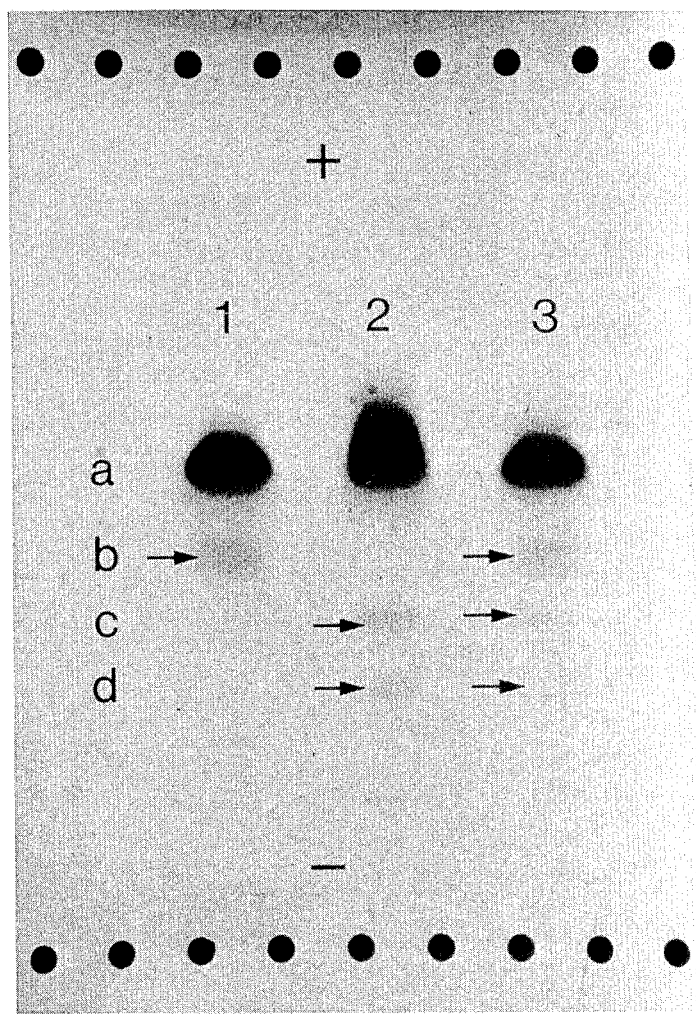

FIG. 3. Electrophoretic pattern on cellulose acetate of SFH before and after AGATP gel chromatography.

Electrophoresis was performed in barbital buffer, pH 8.8. Lanes 1 and 2 are the retained and unretained fractions respectively (see FIG. 1). Lane 3 is a control sample of the starting SFH. Arrows a and b indicate hemoglobin A and its variants, and arrows c and d indicate unidentified minor components of SFH which are enriched in the unretained fraction. Electrophoresis on the Mylar-supported cellulose acetate was run at 200 V for 45 minutes and stained with Ponceau S.

EXAMPLE 1

Purification of Stroma-free Hemoglobin by Agarose-ATP Affinity Chromatography In this example, the source of (oxy)hemoglobin is stroma-free hemoglobin. Agarose-adipic-adenosine-5'-triphospate (AGATP) was prepared by the method of Lamed et al. (Biochem. Biophys. Acta, Vol. 304, p. 231, 1973.) Stroma-free hemoglobin (SFH) was prepared by the method of Rabiner et al. (J. Exp. Med., Vol. 126, p. 1127, 1967). SFH was first dialyzed against 3 changes of 50 mM Bis-Tris buffer, pH 7.0 (Buffer A), and then 500 µl (20 mg) of the SFH solution was then applied to a Pharmacia HR 5/5 column packed with approximately 1 ml of AGATP gel equilibrated with the same buffer. The column was washed with 10 bed volumes of buffer A at a flow rate of 0.5 ml/min until the eluent was clear, and then buffer B (buffer A containing 10 mM ATP) was introduced via a linear gradient to elute the retained fraction. Both the retained and unretained fractions were collected, concentrated, and dialyzed against buffer A. Cellulose acetate elecrophoresis in barbital buffer, pH 8.8 (High Resolution Buffer, Gelman Sciences) was done for each fraction using the starting SFH preparation as a control. For oxygen dissociation studies, a small amount of the red gel was resuspended in 2 µl of buffer A and its oxygen dissociation curve measured using a Hem-O-Scan oxygen dissociation analyzer. As a control, SFH mixed with agarose gel was suspended in solution and its oxygen dissociation curve similarly obtained.

FIG. 1 shows the binding of hemoglobin to the AGATP gel in buffer A, and the selective gradient elution profile resulting from the addition of 10 mM ATP to buffer A. This indicates that hemoglobin is specifically retained via binding of the ATP moiety of the gel to its polyanion binding site. As further evidence of this specificity, SFH is displaced from the gel by the following anions in order of decreasing effectiveness: inositol hexaphosphate $>$ ATP $\simeq$ pyridoxal phosphate $\simeq$ diphosphoglycerate $>$ adenosine diphosphate $>$ phosphate ion $>$ chloride ion (results not shown). FIG. 2 shows a typical oxygen dissociation curve of hemoglobin bound to the AGATP gel. The hemoglobin-AGATP complex is shown to have a $P_{50}$ of 35 mmHg, similar to that of SFH in the presence of four molar equivalents of ATP. By contrast, the control SFH-agarose mixture has a $P_{50}$ of 12 mmHg.

Thus, (oxy)hemoglobin has been shown to have sufficient affinity for AGATP to form a stable complex. Binding of SFH to AGATP lowers the oxygen affinity of SFH to a level equal to that of the soluble SFH-ATP complex, indicating that complex formation is due to specific binding of SFH to the ATP moiety of the gel.

Cellulose acetate electrophoresis of SFH indicates the presence of minor components (FIG. 3), two of which are absent from the retained fraction. Two of these minor bands are enhanced in the unretained fraction (Lane 2) while one is enhanced in the retained fraction (Lane 1). Furthermore, there is an increase in hemoglobin with high electrophoretic mobility in the unretained fraction. Thus, polyanion affinity chromatography is shown to improve the purity and quality of SFH.

It will be appreciated that although the Example 1 employs stroma-free hemoglobin as the source of (oxy)hemoglobin, other sources of (oxy)hemoglobin may also be employed including, used blood (from open-heart surgery, for example), human placental extract, and hemoglobin containing solutions produced by biotechnological methods.

EXAMPLE 2

Purification of glyoxylated hemoglobin by Agarose-ATP affinity chromatography In this example which illustrates the second aspect of the invention, modified glyoxylated hemoglobin (G-Hb) was prepared according to the method of Acharya et al (Fed. Proc., Fed. Amer. Soc. Exp. Biol., Vol. 41, p. 1174, 1982). Hemoglobin concentrations were measured using a Corning 2500 CO-oximeter Agarose-hexane-adenosine-5'-triphosphate (ATP-agarose) (Type 4), containing 9.2 µmoles of ATP per ml of gel, was purchased from Pharmacia P-L Biochemicals. Affinity chromatography of hemoglobin solutions was performed using a Pharmacia Fast Protein Liquid Chromatography system. The experimental conditions used are similar to those described in Example 1 above.

In order to determine whether ATP-agarose affinity chromatography is capable of purifying modified hemoglobin, the hemoglobin glyoxylation mixture (G-Hb reaction mixture) was passed through the column and the fractions characterized as in Example 1 above. This produced a similar elution profile (results not shown) to that reported by Hsia et al (J. Chrom., Vol. 303, pp. 425–428, 1984) showing an unretained peak G-Hb-I and a retained peak G-Hb-II.

The oxygen dissociation curves of the starting solutions and their ATP-agarose fractions showed the following order of $P_{50}$s:

G-Hb-II $<$ G-Hb reaction mixture $<$ G-Hb-I

The $P_{50}$ of G-Hb-I is approximately twice of that of G-Hb-II. This result is, again, similar to those reported by Hsia et al (J. Chrom., Vol. 303, pp. 425–428, 1984). The present result further confirms that the heterogeneity in glyoxylated hemoglobin preparation is due to variation in the extent of glyoxylation. Right shifting of the oxygen dissociation curve is proportional to the extent of glyoxylation. The Agarose-ATP affinity chromatography is thus capable of purifying modified hemoglobin (G-Hb-I) with optimal oxygen affinity.

Thus, this purification technique can be used as a method for the purification of modified hemoglobins in general (e.g. pyridoxal phosphate and ATP modified hemoglobins). The pure modified hemoglobin which results is believed to be a superior starting material for the preparation of hemoglobin-based blood substitute, because it has optimally right shifted oxygen affinity and it is free of vaso constrictive unmodified hemoglobin.

The embodiments of the invention in which an exclusive property of privilege is claimed are defined as follows:

1. A method for the isolation of (oxy)hemoglobin from (oxy)hemoglobin-containing solutions or mixtures, comprising:
   (a) preparing an affinity chromatography gel having bound thereto a ligand group capable of specific binding to the DPG site of hemoglobin; and
   (b) passing the (oxy)hemoglobin-containing solution or mixture through the gel, whereby the (oxy)-hemoglobin is retained in the gel, while other components of the solution or mixture are eluted.

2. A method according to claim 1, wherein the ligand is a polyanion selected from the group consisting of a nucleoside triphosphate, a diphosphoglycerate, an inositol phosphate and an inositol sulphate.

3. A method according to claim 2, wherein the chromatographic gel is selected from the group consisting of agarose gel and silica gel.

4. A method according to claim 3, wherein the polyanion is linked to the chromatographic gel by a cross-linking agent.

5. A method according to claim 4, wherein the cross-linking agent is selected from the group consisting of adipic acid and diaminohexane.

6. A method according to claim 5, wherein the polyanion is adenosine triphosphate.

7. A method according to claim 6, wherein the gel is agarose gel.

8. A method according to claim 7, wherein the cross-linking agent is adipic acid.

9. A method according to claim 1, which includes the additional step of:
  (c) introducing into the chromatographic gel an anion which competes with the polyanion originally in the gel, whereby (oxy)hemoglobin is eluted from the gel.

10. A method according to claim 9, wherein the competing anion in order of decreasing effectiveness is selected from the group consisting of inositol hexaphosphate, adenosine triphosphate, pyridoxal phosphate, diphosphoglycerate, adenosine diphosphate, phosphate ion and chloride ion.

11. A method according to claim 9, wherein the competing anion is introduced along with a buffer which does not interfere with the binding of the hemoglobin to the polyanion.

12. A method according to claim 11, wherein the buffer is Bis-Tris buffer, pH 7.0.

13. A method for the separation of stroma-free (oxy)-hemoglobin from a liquid solution containing stroma-free (oxy)hemoglobin, comprising:
  (a) passing the stroma-free (oxy)hemoglobin containing solution through an affinity chromatography gel having bound thereto a ligand group capable of specific binding to the DPG site of hemoglobin whereby the stroma-free (oxy)hemoglobin is retained in the affinity chromatography gel; and
  (b) introducing into the gel an anion which competes with the ligand group originally in the gel, whereby purified strom-free (oxy)hemoglobin is eluted from the gel.

14. A method according to claim 13, wherein the gel and the stroma-free (oxy)hemoglobin solution both include a suitable buffer which does not interfere with the binding of hemoglobin to the ligand group.

15. A method for the separation of unmodified hemoglobin from a liquid reaction mixture containing modified and unmodified hemoglobin, comprising:
  (a) passing the reaction mixture through an affinity chromatography gel having bound thereto a ligand group capable of specific binding to the DPG site of hemoglobin whereby unmodified hemoglobin is retained in the affinity chromatography gel and introducing into the gel an anion which competes with the ligand group originally in the gel, whereby purified unmodified hemoglobin is eluted from the gel.

16. A method according to claim 15, wherein the affinity chromatography gel is ATP-agarose gel.

17. A method according to claim 16, wherein the competing anion in order of decreasing effectiveness is selected from the group consisting of inositol hexaphosphate, adenosine triphosphate, pyridoxal phosphate, diphosphoglycerate, adenosine diphosphate, phosphate ion and chloride ion.

18. A method according to claim 15, wherein the modified hemoglobin is glyoxylated hemoglobin.

19. A method for the separation of stroma-free hemoglobin from a liquid solution containing stroma-free hemoglobin, comprising:
  (a) providing a chromatographic column;
  (b) packing the column with a chromatographic affinity gel;
  (c) immobilizing a ligand group capable of specific binding to the DPG site of hemoglobin, on the chromatographic gel to form an polyanion/affinity chromatographic gel complex;
  (d) passing the stroma-free hemoglobin-containing solution through the column, whereby the stroma-free hemoglobin is retained in the gel complex and
  (e) introducing into the gel complex an anion which competes with the polyanion ligand originally in the gel complex, whereby purified stroma-free hemoglobin is eluted from the column.

20. A method for the separation of unmodified hemoglobin from a liquid reaction mixture containing modified and unmodified hemoglobin, comprising:
  (a) providing a chromatographic column;
  (b) packing the column with a chromatographic affinity gel;
  (c) immobilizing a ligand group capable of specific binding to the DPG site of hemoglobin, on the chromatographic gel to form a polyanion/affinity chromatographic gel complex;
  (d) passing the reaction mixture through the column, whereby unmodified hemoglobin is retained in the gel complex and modified hemoglobin is eluted from the column; and
  (e) introducing into the gel complex an anion which competes with the polyanion ligand originally in the gel complex, whereby purified unmodified hemoglobin is eluted from the column.

21. A method for the isolation of (oxy)hemoglobin-containing solutions or mixtures, comprising:
  (a) providing a chromatographic column;
  (b) packing the column with a chromatographic affinity gel;
  (c) adding to the gel a ligand group capable of specific binding to the DPG site of hemoglobin, to form an polyanion/ligand affinity gel complex; and
  (d) passing the (oxy)hemoglobin solution or mixture through the column, whereby (oxy)hemoglobin is retained in the gel complex and other components of the solution or mixture are eluted from the column.

22. A method according to claim 21, wherein the polyanion ligand is adenosine triphosphate.

23. A method according to claim 22, wherein the gel is agarose gel.

24. A method according to claim 23, where the adenosine triphosphate is linked to the agarose gel by adipic acid.

25. A method according to claim 24, which includes the additional step of:
  (e) introducing into the adenosine triphosphate/agarose gel/(oxy)hemoglobin complex an anion which competes with adenosine triphosphate originally linked to the agarose gel, whereby (oxy)-hemoglobin is eluted from the gel complex and the column.

26. A method according to claim 25, wherein the competing anion is introduced along with Bis-Tris buffer, pH 7.0.

* * * * *